Figure 1:
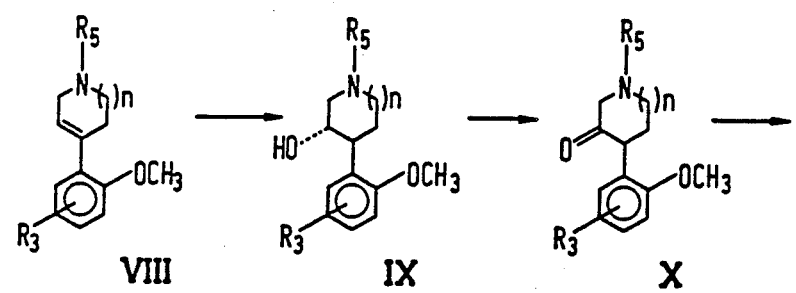
Figure 1:
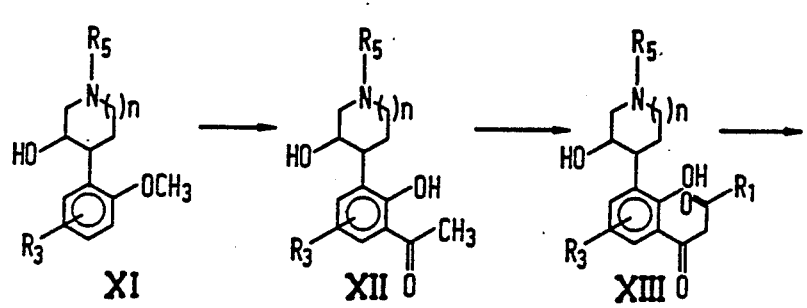
Figure 1:
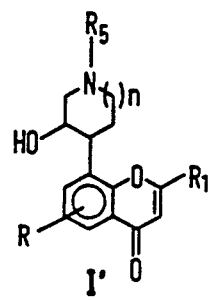

United States Patent [19]

Kattige et al.

[11] Patent Number: 4,900,727

[45] Date of Patent: Feb. 13, 1990

[54] 4H-1-BENZOPYRAN-4-ONE COMPOUNDS WHICH HAVE ANTI-INFLAMATORY OR IMMUNODULATING ACTION

[75] Inventors: Samba L. Kattige; Ramchandra G. Naik; Aftab D. Lakdawalla; Alihussein N. Dohadwalla; Richard H. Rupp; Noel J. de Souza, all of Bombay, India

[73] Assignee: Hoechst Aktiengesellschaft, Frankfurt, Fed. Rep. of Germany

[21] Appl. No.: 302,084

[22] Filed: Jan. 26, 1989

Related U.S. Application Data

[63] Continuation of Ser. No. 36,478, Apr. 9, 1987, abandoned.

[30] Foreign Application Priority Data

Apr. 11, 1986 [DE] Fed. Rep. of Germany ....... 3612337

[51] Int. Cl.$^4$ .................. A61K 31/445; C07D 405/04
[52] U.S. Cl. .................................... 514/212; 514/318; 514/320; 514/336; 514/422; 546/193; 546/196; 546/269; 540/596; 548/525
[58] Field of Search ....... 546/193, 196, 269; 548/525; 540/596; 549/401; 514/212, 318, 320, 336, 422

[56] References Cited

U.S. PATENT DOCUMENTS 4,603,137 7/1986 Bhat et al. ........................ 546/196

OTHER PUBLICATIONS

Mar.; Advanced Organic Chemistry; pp. 439; 791.
Chemical Abstracts, vol. 91, No. 13, Abstract: 108119p, p. 597, 9/24/79.

*Primary Examiner*—Mary C. Lee
*Assistant Examiner*—Zinna Northington-Davis
*Attorney, Agent, or Firm*—Finnegan, Henderson, Farabow, Garrett and Dunner

[57] ABSTRACT

The present invention relates to novel 4H-1-benzopyran-4-one derivatives, to processes for the preparation thereof and to their use as anti-inflammatory, analgesic, immuno-suppressive and anti-allergic agents. In particular, the present invention relates to novel compounds of the formula I,

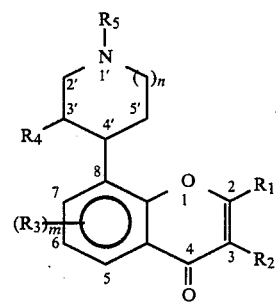

in which $R_1$ is hydrogen, alkyl having 1 to 6 carbon atoms, arly-$C_1$-$C_4$-alkyl, substituted $C_1$-$C_6$-alkyl, $C_3$-$C_6$-cycloalkyl, $C_3$-$C_6$-cycloalkyl-$C_1$-$C_4$-alkyl, $C_2$-$C_6$-alkenyl, $C_3$-$C_6$-alkynyl, aryl or carboxyl or an aldehyde or COO—$C_1$-$C_4$-alkyl group, $R_2$ is hydrogen, alkyl having 1 to 6 carbon atoms, nitro, amino, di-$C_1$-$C_4$-alkylamino or a halogen, $R_3$ is $C_1$-$C_4$-alkyl, substituted $C_1$-$C_4$-alkyl, hydroxyl, $C_1$-$C_4$-alkoxy, aryl-$C_1$-$C_4$-alkyl, nitro, amino, a $C_1$-$C_4$-alkylamino or di-$C_1$-$C_4$-alkylamino group or halogen, $R_4$ is hydrogen, hydroxyl, $C_1$-$C_4$-alkyoxy, $C_1$-$C_4$-alkyoxycarbonyl, aryloxy, amino or a $C_1$-$C_4$-alkylamino or di-$C_1$-$C_4$-alkylamino group, $R_5$ is hydrogen, $C_1$-$C_6$-alkyl, substituted $C_1$-$C_6$-alkyl, aryl-$C_1$-$C_4$-alkyl, $C_3$-$C_6$-cycloalkyl, $C_3$-$C_6$-cycloalkyl-$C_1$-$C_4$-alkyl, $C_1$-$C_4$-alkanoyl or aroyl, the aryl group being phenyl which is unsubstituted, monosubstituted or polysubstituted, m is an integer between 0 and 3 and n is an integer between 0 and 2, and to pharmacologically acceptable acid addition salts thereof.

12 Claims, 3 Drawing Sheets

4H-1-BENZOPYRAN-4-ONE COMPOUNDS WHICH HAVE ANTI-INFLAMATORY OR IMMUNODULATING ACTION

This application is a continuation of application Ser. No. 07/036,478 filed April 9, 1987, now abandoned.

The present invention relates to novel 4H-1-benzopyran-4-one derivatives, to processes for the preparation thereof and to their use as anti-inflammatory, analgesic, immunosuppressive and anti-allergic agents. In particular, the present invention relates to novel compounds of the formula I

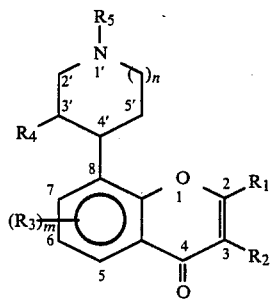

in which
$R_1$ is hydrogen, alkyl having 1 to 6 carbon atoms, aryl-$C_1$-$C_4$-alkyl, substituted $C_1$-$C_6$-alkyl, $C_3$-$C_6$-cycloalkyl, $C_3$-$C_6$-cycloalkyl-$C_1$-$C_4$-alkyl, $C_2$-$C_6$-alkenyl, $C_3$-$C_6$-alkynyl, aryl, carboxyl or an aldehyde or COO-$C_1$-$C_4$-alkyl group, $R_2$ is hydrogen, alkyl having 1 to 6 carbon atoms, nitro, amino, di-$C_1$-$C_4$-alkylamino or a halogen, $R_3$ is $C_1$-$C_4$-alkyl, substituted $C_1$-$C_4$-alkyl, hydroxyl, $C_1$-$C_4$-alkoxy, aryl-$C_1$-$C_4$-alkyl, nitro, amino, a $C_1$-$C_4$-alkylamino or di-$C_1$-$C_4$-alkylamino group or halogen, $R_4$ is hydrogen, hydroxyl, $C_1$-$C_4$-alkoxy, $C_1$-$C_4$-alkanoyloxy, $C_1$-$C_4$-alkoxycarbonyl, aryloxy, amino or a $C_1$-$C_4$-alkylamino or di-$C_1$-$C_4$-alkylamino group, $R_5$ is hydrogen, $C_1$-$C_6$-alkyl, substituted $C_1$-$C_6$-alkyl, aryl-$C_1$-$C_4$-alkyl, $C_3$-$C_6$-cycloalkyl, $C_3$-$C_6$-cycloalkyl-$C_1$-$C_4$-alkyl, $C_1$-$C_4$-alkanoyl or aroyl, the aryl group being phenyl which is unsubstituted or mono or polysubstituted, m is an integer between 0 and 3 and
n is an integer between 0 and 2,
and to pharmacologically acceptable acid addition salts thereof.

The compounds according to the invention have two asymmetric centers, one being at the linkage point of the nitrogen heterocyclic ring with the benzopyran moiety (C-4') and the other being at the carbon atom (C-3') substituted by $R_4$, so that two pairs of optical isomers are possible. It is to be understood that the definition of the compounds according to the invention includes all possible stereo isomers and their mixtures. In particular, both the racemic forms and the isolated optical isomers having the indicated activity are included. The two racemates can be resolved by physical methods such as fractional crystallization. The individual optical isomers are obtainable from the racemates by standard methods such as formation of the salt with an optically active acid and subsequent crystallization.

In EP-A2-0,137,193, the compound 5,7-dihydroxy-2-methyl-8-[4'-(3'-hydroxy-1'-methyl)-piperidinyl]-4H-1-benzopyran-4-one in the trans−(+)−form, its isolation from the plant Dysoxylum binectariferum and its use as an agent for immunomodulation have already been described. This racemate compound is therefore excepted from the present invention.

Examples of suitable alkyl groups $R_1$-$R_5$ are straight-chain or branched radicals having up to 6 and preferably up to 5 carbon atoms, for example methyl, ethyl, propyl, isopropyl, t-butyl, pentyl or isopentyl groups.

Examples of suitable substituted alkyl groups $R_1$-$R_5$ are halogenoalkyl such as trifluoromethyl, hydroxyalkyl such as hydroxyethyl or carboxyalkyl such as carboxyethyl.

Suitable examples of a cycloalkyl group $R_1$ and $R_5$ having 3 to 6 carbon atoms are cyclopropyl, cyclobutyl, cyclopentyl or cyclohexyl. Cyclopropylmethyl is an example of cycloalkylalkyl.

An example of an aralkyl group $R_1$ and $R_5$ is a phenylalkyl group in which the phenyl group is unsubstituted or mono- or poly-substituted by substituents such as halogen, $C_1$-$C_4$-alkyl, $C_1$-$C_4$-alkoxy, nitro or a trifluoromethyl group.

An example of an aryl group $R_1$ and $R_5$ is a phenyl group which is unsubstituted or mono- or poly-substituted by substituents such as halogen, $C_1$-$C_4$-alkyl, $C_1$-$C_4$-alkoxy, nitro or trifluoromethyl.

A suitable example of alkylamino $R_1$ and $R_5$ is $(CH_2)_n$-$NR_6R_7$, n being 1-3, and $R_6$ and $R_7$ being alkyl having the same meaning as that of alkyl $R_1$-$R_5$ above; moreover, $R_6$ and $R_7$, together with the nitrogen atom to which they are attached, can be a heterocyclic ring having one or more heteroatoms. Suitable examples of heterocyclic rings formed by $R_6$ and $R_7$, together with the nitrogen to which they are attached, are piperidine, pyrrolidine, morpholine, piperazine or imidazole, which can be unsubstituted or substituted in one or more positions by $C_1$-$C_4$-alkyl, $C_1$-$C_4$-alkoxy, aryl or a hydroxyl or amino group.

Suitable examples of salts of the compounds according to the invention with inorganic or organic acids are the hydrochloride, hydrobromide, sulfate, phosphate, acetate, oxalate, tartrate, citrate, maleate or fumarate.

Preferred compounds are of the formula Ia

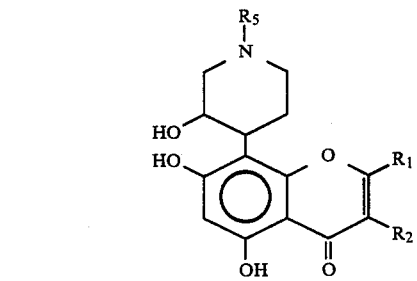

in which
$R_1$, $R_2$ and $R_5$ are as defined above and in particular:
$R_1$ is hydrogen or $C_1$-$C_3$-alkyl,
$R_2$ is hydrogen or $C_1$-$C_3$-alkyl and
$R_5$ is $C_1$-$C_3$-alkyl or $C_3$-$C_5$-cycloalkyl.

Particularly preferred compounds according to the invention are:
cis-(−)-5,7-dihydroxy-2-methyl-8-[4'-(1'-cyclopropylmethyl-3'-hydroxy)-piperidinyl]-4H-1-benzopyran-4-one,
cis-(+)-5,7-dihydroxy-2-methyl-8-[4'-(3'-hydroxy-1'-methyl)-piperidinyl]-4H-1-benzopyran-4-one, cis-(−)-5,7-dihydroxy-2-methyl-8-[4'-(3'-hydroxy-1'-methyl)-piperidinyl]-4H-1-benzopyran-4-one,
cis-(±)-5,7-dihydroxy-2-methyl-8-[4'-3'-hydroxy-1'-methyl)-piperidinyl]-4H-1-benzopyran-4-one,
cis-(±)-5,7-dihydroxy-2-ethyl-8-[4'-3'-hydroxy-1'-methyl)-piperidinyl]-4H-1-benzopyran-4-one,
cis-(±)-5,7-dihydroxy-2-n-propyl-8-[4'-(3'-hydroxy-1'-methyl)-piperidinyl]-4H-1-benzopyran-4-one,
cis-(+)-5,7-dihydroxy-2-n-propyl-8-[4'-(3'-hydroxy-1'-methyl)-piperidinyl]-4H-1-benzopyran-4-one,
cis-(−)-5,7-dihydroxy-2-n-propyl-8-[4'-(3'-hydroxy-1'-methyl)-piperidinyl]-4H-1-benzopyran-4-one,
cis-(±)-2-n-butyl-5,7-dihydroxy-8-[4'-(3'-hydroxy-1'-methyl)-piperidinyl]-4H-1-benzopyran-4-one,
cis-(±)-5,7-dihydroxy-2-phenyl-8-[4'-(3'-hydroxy-1'-methyl)-piperidinyl]-4H-1-benzopyran-4-one,
cis-(−)-5,7-dihydroxy-2-phenyl-8-[4'-(3'-hydroxy-1'-methyl)-piperidinyl]-4H-1-benzopyran-4-one,
cis-(±)-2-(2-chlorophenyl)-5,7-dihydroxy-8-[4'-3'-hydroxy-1'-methyl)-piperidinyl]-4H-benzopyran-4-one,
cis-(−)-2-(2-chlorophenyl)-5,7-dihydroxy-8-[4'-(3'-hydroxy-1'-methyl)-piperidinyl]-4H-1-benzopyran-4-one,
cis-(±)-2-(4-aminophenyl)-5,7-dihydroxy-8-[4'-(3'-hydroxy-1'-methyl)-piperidinyl]-4H-1-benzopyran-4-one,
cis-(±)-2-(4-bromophenyl)-5,7-dihydroxy-8-[4'-(3'-hydroxy-1'-methyl)-piperidinyl]-4H-1-benzopyran-4-one,
cis-(±)-2-(4-chlorophenyl)-5,7-dihydroxy-8-[4'-(3'-hydroxy-1'-methyl)-piperidinyl]-4H-1-benzopyran-4-one,
cis-(±)-2-(2,4-dichlorophenyl)-5,7-dihydroxy-8-[4'-(3'-hydroxy-1'-methyl)-piperidinyl]-4H-1-benzopyran-4-one,
cis-(±)-5,7-dihydroxy-2-(4-fluorophenyl)-8-[4'-(3'-hydroxy-1'-methyl)-piperidinyl]-4H-1-benzopyran-4-one,
cis-(±)-5,7-dihydroxyl-2-(2-fluorophenyl)-8-[4'-(3'-hydroxy-1'-methyl)-piperidinyl]-4H-1-benzopyran-4-one,
cis-(±)-5,7-dihydroxy-2-(4-methylphenyl)-8-[4'-(3'-hydroxy-1'-methyl)-piperidinyl]-4H-1-benzopyran-4-one,
cis-(±)-5,7-dihydroxy-2-(2-pyridyl)-8-[4'-(3'-hydroxy-1'-methyl)-piperidinyl]-4H-1-benzopyran-4-one,
cis-(±)-5,7-dihydroxy-2-(4-pyridyl)-8-[4'-(3'-hydroxy-1'-methyl)-piperidinyl]-4H-1-benzopyran-4-one.

Novel 4-H-1-benzopyran-4-one derivatives according to the invention are listed in Tables 1 to 5 below, reference being made to the following formulae:

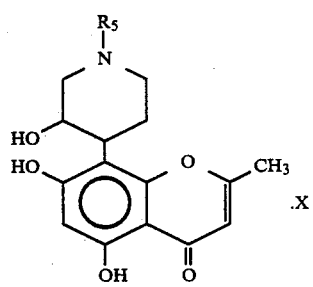

Formula Ib

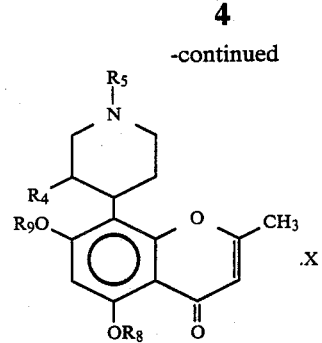

Formula Ic

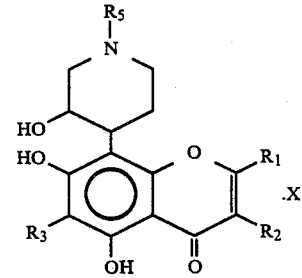

Formula Id

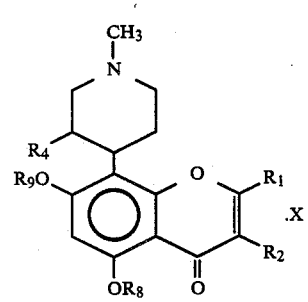

Formula Ie

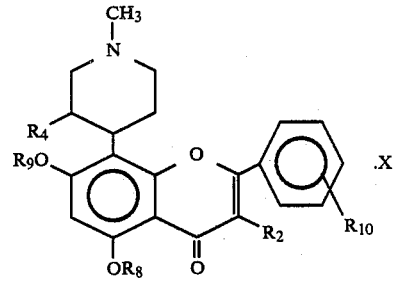

Formula If

TABLE 1

Compounds of formula Ib

| $R_5$ | Melting point of the base | X | Melting point of the salt |
|---|---|---|---|
| H | >300° | — | — |
| CN | 212–14° | — | — |
| $CH_3$ | — | HCl.½H$_2$O | 253–57° |
| $C_2H_5$ | — | HCl.H$_2$O | >300° |
| $CH_2CH_2CN$ | 200–2° | — | — |
| p-Cl—C$_6$H$_4$—C(O)— | — | H$_2$O | 178–80° |
| $C_6H_4$—CH$_2$— | 214–16° | — | — |
| $(CH_2)_2CH(CH_3)_2$ | — | HCl.3H$_2$O | 265–68° |
| $CH_2COOK$ | — | 4.H$_2$O | 250–53° (Decomp.) |
| —C(O)—CH$_2$COOCH$_3$ | — | H$_2$O | 185–88° |

TABLE 1-continued

Compounds of formula Ib

| R5 | Melting point of the base | X | Melting point of the salt |
|---|---|---|---|
| $CH_2-CH=CH_2$ | — | HCl | 235-38° |
| p-F—$C_6H_4$—$CH_2$ | — | HCl | 260-63° |
|  | 236-39° | — | — |
| p-F—$C_6H_4$—NH—C(=O)— | — | HCl.1½H$_2$O | 224-26° |
| p-CN—$C_6H_4$—$CH_2$ | — | — | — |
| $CH_2CH_2OH$ | — | $CH_3OH$ | 202-5° |
| m-$CF_3$—$C_6H_4$—$CH_2$ | — | HCl.1½H$_2$O | 173-75° |
| $C_6H_5$—C(=O)—$CH_2$ | — | HCl.½H$_2$O | >200° |
| $C_6H_{11}$ | — | HCl.1½H$_2$O | >220° |
| $CH(CH_3)_2$ | >210 | — | — |
| 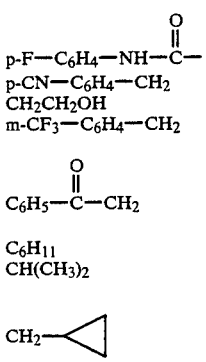 $CH_2$—cyclopropyl | — | HCl.H$_2$O | >210 |

| R5 | Melting point of the base | X | Melting point of the salt |
|---|---|---|---|
| $CH_3$ | — | cis(+)HCl | 242-43° |

TABLE 2

Compounds of the formula Ic

| R4 | R5 | R8 | R9 | X | Melting point |
|---|---|---|---|---|---|
| $OCOCH_3$ | CN | $COCH_3$ | $COCH_3$ | — | 207-9° |
| $OCH_2CH=CH_2$ | $CH_2CH=CH_2$ | H | H | HCl | 235-38° |
| OH(cis) | $CH_2CO_2C_2H_5$ | H | $CH_2CO_2C_2H_5$ | H$_2$O | 185-88° |
| OH(trans) | $CH_3$ | H | H | HCl.½H$_2$O | >290° |
| C—$CH_2$—$C_6H_5$ | $CH_3$ | H | H | — | 238-40° |
| O—C(=O)—$CH_3$ | $CH_3$ | $COCH_3$ | H | HCl.2H$_2$O | 192-94° |
| O—C(=O)—$CH_3$ | $CH_3$ | H | H | HCl | 195-99° |
| OH | $CH_3$ | $SO_2NH_2$ | H | $H_2SO_4$.2½H$_2$O | 277-80° |
| OH(trans) | $CH_3$ | $CH_3$ | $CH_3$ | — | >250 |
| OH(cis) | $CH_3$ | $CH_3$ | $CH_3$ | — | 236-39° |
| OH(cis) | $C_2H_5$ | $CH_3$ | $CH_3$ | HCl.½H$_2$O | 240-42° |
| OH(cis) | $CH_3$ | H | $CH_3$ | HCl | 230-32° |

TABLE 3

Compounds of the formula Id

| R1 | R2 | R3 | R5 | X | Melting point |
|---|---|---|---|---|---|
| $CH_3$ | H | Br | $CH_3$ | HCl | >300° |
| $CH_3$ | $CH_2N(CH_3)_2$ | Br | $CH_3$ | 2HCl.2H$_2$O | >300° |
| $CH_3$ | $NO_2$ | H | $CH_3$ | HCl.1½H$_2$O | 272-75° (Decomp.) |
| $CH_3$ | Br | H | $CH_3$ | — | 275-76° |
| $CH_3$ | $NH_2$ | H | $CH_3$ | HCl.H$_2$O | 197-200° |
| H | H | H | $CH_3$ | — | 298° (Decomp.) |
| $C_2H_5$ | H | H | $CH_3$ | HCl.1½H$_2$O | 230-33° |
| n-$C_3H_7$ | H | H | $CH_3$ | HCl.H$_2$O | 190-92° |

TABLE 4

Compounds of the formula Ie

| R1 | R2 | R4 | R8 | R9 | X | Melting point | Optical rotation |
|---|---|---|---|---|---|---|---|
| H | H | OH | H | H | — | 298° (Decomp.) | (±) |
| H | H | OH | $CH_3$ | $CH_3$ | HCl, 1.5H$_2$O | 173-175 | (±) |
| $CH_3$ | H | OH | H | H | HCl, | 237-240 | (±) |
| $CH_3$ | H | OH | H | H | HCl | 243-43 | (±) |
| $CH_3$ | H | OH | H | H | HCl | 241-42 | (−) |
| $CH_3$ | H | OH | H | $CH_3$ | HCl | 230-232 | (±) |
| $CH_3$ | H | OH | $CH_3$ | $CH_3$ | 2HCl.2H$_2$O | 236-239 | (±) |
| $CH_3$ | H | H | H | H | H$_2$O | 232-233 | (±) |
| $C_2H_5$ | H | OH | H | H | HCl, 1.5H$_2$O | 230-233 | (±) |
| $C_2H_5$ | H | OH | $CH_3$ | $CH_3$ | HCl, 1.5H$_2$O | 240-242 | (±) |
| n-$C_3H_7$ | $CH_3$ | OH | H | H | — | 191-192 | (±) |
| n-$C_3H_7$ | H | OH | H | H | HCl | 190-192 | (±) |
| n-$C_3H_7$ | H | OH | H | H | HCl, 0.5H$_2$O | 197-200 | (+) |
| n-$C_3H_7$ | H | OH | H | H | HCl, 0.5H$_2$O | 198-201 | (−) |
| n-$C_4H_9$ | H | OH | H | H | HCl, H$_2$O | 157-159 | (±) |
| $CH_3$ | $CH_3$ | OH | H | H | H$_2$O | 232-233 | (±) |

TABLE 5

Compounds of the Formula If

| R10 | R8 | R9 | X | Melting point | Optical rotation |
|---|---|---|---|---|---|
| H | H | H | HCl, 2H$_2$O | 273-275° | (±) |
| 4-$NO_2$ | H | H | HCl, 3H$_2$O | 249° (Decomp.) | (±) |

TABLE 5-continued

Compounds of the Formula If

| $R_{10}$ | $R_8$ | $R_9$ | X | Melting point | Optical rotation |
|---|---|---|---|---|---|
| 4-$NO_2$ | $CH_3$ | $CH_3$ | HCl, 2$H_2O$ | 257–260° (Decomp.) | (±) |
| 2-Cl | H | H | HCl, $H_2O$ | 198–200° | (±) |
| 2-Cl | $CH_3$ | $CH_3$ | 1.5HCl, $H_2O$ | 190–191° | (±) |
| 4-$NH_2$ | H | H | 2HCl, 2$H_2O$ | 240–242 | (±) |
| 3,5-Dimethoxy | $CH_3$ | $CH_3$ | 2HCl, 2$H_2O$ | 180–182° | (±) |
| 4-Br | H | H | HCl, 2$H_2O$ | 215° | (±) |
| 4-Cl | H | H | HCl, 1.5$H_2O$ | 225° | (±) |
| 2,4-Dichloro | H | H | HCl, 2.5$H_2O$ | 165–166 | (±) |
| 4-F | H | H | HCl, $H_2O$ | 285–287° | (±) |
| 2-F | H | H | HCl, 2$H_2O$ | 263–265 | (±) |
| 4-Methyl | H | H | HCl, 1.5$H_2O$ | 247–49 | (±) |
| 3,5-Dihydroxy | H | H | HCl, 3$H_2O$ | 300–302 | (±) |
| 3-Cl | H | H | HCl, 2$H_2O$ | 288–290 | (±) |
| 3-Methyl | H | H | HCl, 2$H_2O$ | 268° | (±) |
| 2-Methyl | H | H |  | 204–205 | (±) |
| 2-Cl | H | H | HCl, 2$H_2O$ | 190–192 | (+) |
| H | H | H | HCl, | 269–271 | (±) |
| 3-Br | H | H | HCl, 2$H_2O$ | 285° | (±) |
| 3-$CO_2$Me | $CH_3$ | $CH_3$ | 1.5HCl, 3$H_2O$ | 235° | (±) |
| 2,5-Dichloro | H | H | HCl, $H_2O$ | 251–252 | (±) |
| 3-COOH | $CH_3$ | $CH_3$ | HCl, 1.5$H_2O$ | 270 | (±) |
| 2-Cl | H | H | HCl, 1.5$H_2O$ | 190–194 | (−) |
| H | H | H | HCl, 0.5$H_2O$ | 266–69 | (−) |

The present invention also relates to a process for preparing compounds of the general formula I, which process comprises the steps sketched in the scheme in the attached FIG. 1. If desired, further chromone derivatives according to the invention can be obtained by treating compounds of the formula I' in FIG. 1 by known methods. The general scheme illustrated in FIG. 1 is explained and described in more detail by the reaction sequence illustrated in FIG. 2, which relates to the preparation of one of the preferred compounds according to the invention; it is here to be understood that the scope of the invention is not restricted thereby.

The preparation of the compound of the formula VIII with n=1 is known to those skilled in the art [S. M. McClavain and R. S. Berger, J. Am. Chem. Soc., 77, 2848 (1955); A. Ziering, L. Berger, S. D. Heineman and J. Lec., J. Org. Chem., 12, 894 (1947)]. Two methods are described in these papers. In the first method, 1,3,5-trimethoxybenzene is stirred with n-butyllithium at low temperatures, preferably between −60° and −90° C., in inert solvents such as hydrocarbons, for example pentane or hexane, or ether solvents, for example diethyl ether or tetrahydrofuran, to prepare the lithio salt which, on stirring with 1-methyl-4-piperidone and subsequent acidification, gives the tetrahydropyridine derivative. In the second and particularly preferred method, 1,3,5-trimethoxybenzene is stirred under acid conditions with 1-methyl-4-piperidone in solvents such as water, acetic acid, alcoholic solvents or a suitable mixture thereof, glacial acetic acid being particularly preferred.

Figure 2:
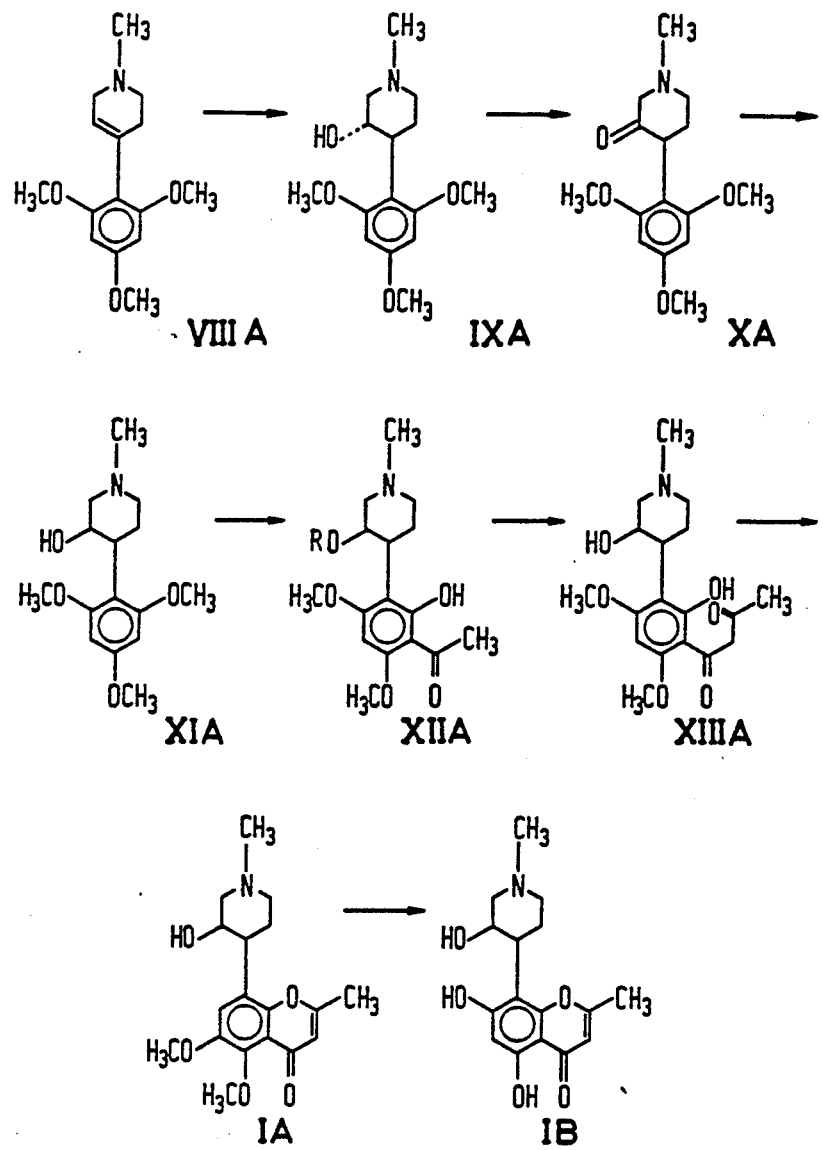

Referring to the scheme in FIG. 2, the tetrahydropyridine derivative of the illustrated formula VIII (i.e. formula VIII with n=1) is hydroborinated, using diborane which forms directly by adding $BF_3$ etherate to a suspension of sodium borohydride in diethylene glycol dimethyl ether under anhydrous conditions and in an inert atmosphere maintained by continuously passing nitrogen or argon through. The reaction temperature is maintained between 20° and 90° C., but a temperature range of 50°–60° C. is preferred. The resulting organoborane complex is first treated with hydrochloric acid and then oxidized by addition of alkali and hydrogen peroxide. The compound thus obtained is a trans-alcohol of the formula IXA and this is converted by oxidation and subsequent reduction into the cis-alcohol of the formula XIA. The oxidation of the trans-alcohol of the formula IXA is carried out by means of a combination of reagents, namely acid chlorides, oxalyl chloride being preferred, dimethyl sulfoxide and triethylamine, and this is known to those skilled in the art as an oxidation by the method of Swern. The ketone of the formula XA, formed by oxidation of the compound of the formula IXA, is reduced by means of hyrdide reagents, preferably diborane, lithium borohydride or sodium borohydride. A fair number of solvents are compatible with sodium borohydride, but protic solvents such as methanol, ethanol and isopropanol are preferred. The cis-isomer can be obtained stereoselectively by maintaining a higher reaction temperature.

The cis-isomer can also be obtained by fractional crystallization of its acid addition salts which are formed with optically active acids such as, for example, (−)-and/or (+)-dibenzoyl tartaric acid.

If desired, the cis-isomer can also be esterified with an optically active acid such as (−)-menthyloxyacetic acid, and the resulting diestereomeric esters can then be separated by conventional methods such as fractional crystallization or chromatography.

The cis-hydroxy compound of the formula XIA is acetylated with acetic anhydride and acid catalysts such as aluminum chloride, boron trifluoride etherate and tin(IV) chloride, the particularly preferred reagent being boron trifluoride etherate. When using a large excess of boron trifluoride etherate, demethylation also takes place simultaneously, and only the desired methoxy group is demethylated regiospecifically, a compound of the formula XIIA being obtained, in which R is the radical —$COCH_3$. The hydrolysis of this compound with an alkali metal hydroxide leads to compounds of the formula XIIA with R=H. The compound of the formula XIIA is then converted into the chromone by methods known per se, of which two are described here. In the first method, the compound of the formula XIIA with R=H is stirred at room temperature in inert solvents, such as ether, tetrahydrofuran, dioxane or hydrocarbon solvents such as hexane, with ethyl acetate and an alkali metal or NaH, preferably sodium metal; if the ester is a low-boiling liquid as in the present example, it can also be used as the solvent. The reaction is normally complete after one to ten hours and gives the diketone of the formula XIIIA with R=H, which is cyclized to give the chromone of the formula IA on stirring with mineral acids such as hydrochloric acid or sulfuric acid. In the second method, a compound of the formula XIIA is esterified with R=Ac, using a suitable acid, for example benzoic acid, and the resulting ester is stirred with a base such as, for example, an alkali metal hydroxide, in an inert solvent such as, for example, THF, dioxane or pyridine, the chromone of the formula IA being formed. The latter is demethoxylated with pyridine hydrochloride, in order to obtain the hydroxy compound of the illustrated formula IB. Using the corresponding esters in place of ethyl acetate, various 2-substituted chromones can be prepared.

In place of $AlCl_3$, $BBr_3$ or $HBr$/acetic acid, other acid reagents can also be used for demethoxylating the dimethoxychromone of the formula IA. The demethoxylation is effected by heating the dimethoxychromone derivatives with pyridine hydrochloride for a period of 2 to 10 hours to 180° C. In some cases, an addition of high-boiling amines to the pyridine hydrochloride can be advantageous.

Figure 3:
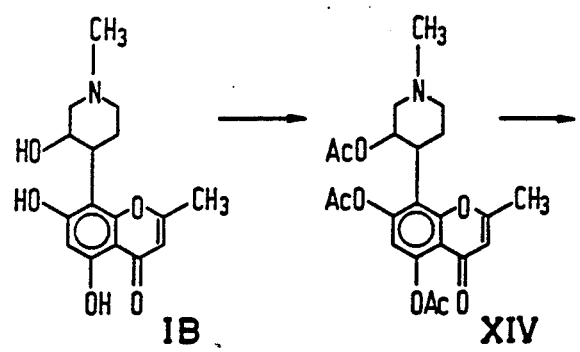
Figure 3:
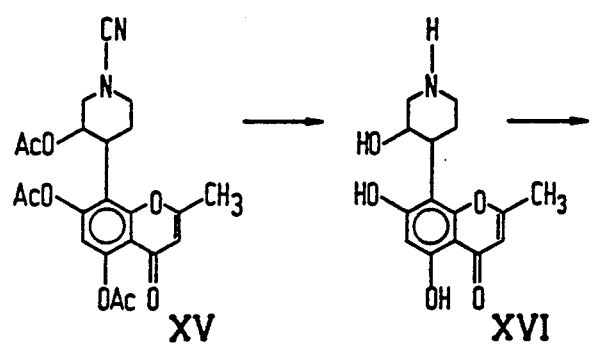
Figure 3:
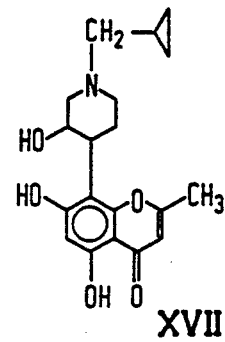

The synthesis scheme according to FIG. 2 can be applied for the preparation of compounds of the formula I with $R_5$=H, alkyl (other than methyl), cycloalkyl, aralkyl and aryl. Compounds of the formula I, in which $R_5$ is as defined above, can also be prepared from the corresponding N-methyl compounds, i.e. $R_5$=$CH_3$ (compounds of the formula IB), by one of the known methods. A typical procedure can be seen from the scheme in FIG. 3, where a compound of the formula IB with $R_5$=$CH_3$, after protection of the hydroxyl groups, is treated with cyanogen bromide and then hydrolyzed under acidic or alkaline conditions to give compounds with $R_5$=H (compound of the formula XIV). On treatment with suitable electrophilic reagents, such as halides, acid chlorides, tosylates or enones, this compound gives compounds with $R_5$=alkyl, cycloalkyl, aralkyl or aryl, the compound of the illustrated formula XVII being a specific example. According to FIG. 3, 5,7-dihydroxy-2-methyl-8-[4'-(1'-cyclopropylmethyl-3'-hydroxy)-piperidinyl]-4H-1-benzopyran-4-one of the illustrated formula XVII is prepared by peracetylating 5,7-dihydroxy-2-methyl-8-[4'-(3'-hydroxy-1'-methyl)-piperidinyl]-4H-1-benzopyran-4-one of the formula IB with acetic anhydride and sodium acetate at 80°-90° C. The peracetylated product of the formula XIV is stirred with cyanogen bromide in chloroform and, in the presence of potassium carbonate, gives 5,7-diacetyl-2-methyl-8-[4'-(3'-acetoxy-1'-cyan)-piperidinyl]-4H-benzopyran-4-one of the formula XV, which, when heated for 5 hours with 2N hydrochloric acid to 110° C., gives the hydrolyzed and N-demethylated product 5,7-dihydroxy-2-methyl-8-[4'-(3'-hydroxy)-piperidinyl]-4H-1-benzopyran-4-one of the formula XVI. On heating with cyclopropylmethyl chloride in isobutyl alcohol, this gives the N-cyclopropylmethyl derivative of the illustrated formula XVII.

Compounds of the formula I, in which $R_2$ is dialkylaminomethyl, are prepared by heating under reflux the corresponding chromone, where $R_2$=H, with a secondary amine hydrochloride and paraformaldehyde in dioxane or alcoholic solvents. Compounds of the formula I with $R_2$=$NO_2$ are appropriately prepared by stirring the corresponding chromone, where $R_2$=H, with acetic acid and concentrated nitric acid. Compounds of the formula I with $R_2$=$NH_2$ are obtained from the corresponding nitro derivatives by hydrogenation over 10% Pd/C.

Compounds of the formula I, in which one of the $R_3$ groups is bromine, are prepared by stirring the corresponding chromones, where $R_3$=H, with N-bromosuccinimide in dimethylformamide.

It is a further feature of the invention that the compounds according to the invention, represented by the formula I, possess pharmacological properties. In particular, they show an anti-inflammatory and immunomodulating action on laboratory animals. These properties are demonstrated by the results of the pharmacological tests which follow and which were carried out for evaluating the compounds according to the invention and their salts.

Systemic anti-inflammatory action on carrageenin-induced paw edema in rats

Male Charles Foster rats (120-150 g) were fasted for 18 hours, with water ad libitum. The test compound dissolved in distilled water was administered orally. The control group received distilled water. 0/05 ml of 0.5% carrageenin suspension was injected subcutaneously into the plantar region of the left hind paw. Using a Maclab differential volume meter, the paw volume was determined before the carrageenin injection and 3 and 6 hours after the injection. The percentage decrease in paw volume was calculated by the following equation:

$$\frac{\text{Vehicle control mean edema volume} - \text{Test group mean edema volume}}{\text{Vehicle control mean edema volume}} \times 100 =$$

% decrease in paw volume

The $ED_{50}$ value was calculated from the dose/response curve. Six animals were used for each group.

The results with representative compounds according to the invention and their salts are listed in Table 4, the substituents relating to the following formula Ia:

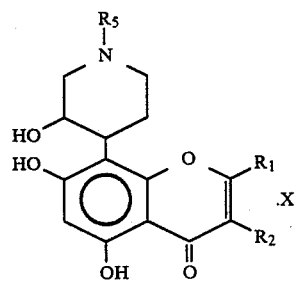

TABLE 6

Compounds of the formula Ia

| cis | R$_1$ | R$_2$ | R$_5$ | X | ED$_{50}$ mg/kg p.o. |
|---|---|---|---|---|---|
| (−) | CH$_3$ | H | —CH$_2$—◁ | HCl.H$_2$O | 10.0 |
| (+) | CH$_3$ | H | CH$_3$ | HCl | 9.4 |
| (−) | CH$_3$ | H | CH$_3$ | HCl | 9.0 |
| (±) | CH$_3$ | H | CH$_3$ | HCl | 12.5 |
| (±) | C$_2$H$_5$ | H | CH$_3$ | HCl.1.5 H$_2$O | 10.5 |
| (±) | n-C$_3$H$_7$ | H | CH$_3$ | HCl.H$_2$O | 6.8 |
| (−) | n-C$_3$H$_7$ | H | H | HCl, 5 H$_2$O | 5.8 |
| (±) | Phenyl | H | H | HCl, 2 H$_2$O | 5.7 |
| (±) | 2-chlorophenyl | H | H | HCl, H$_2$O | 2.7 |
| (±) | 4-Aminophenyl | H | H | 2HCl, 2 H$_2$O | 7.4 |
| (±) | 4-chlorophenyl | H | H | HCl, 1.5 H$_2$O | 7.0 |
| (±) | 2,4-dichlorophenyl | H | H | HCl, 2.5 H$_2$O | 5.7 |
| (±) | 4-fluorophenyl | H | H | HCl, H$_2$O | 7.4 |
| (±) | 2-fluorophenyl | H | H | HCl, 2 H$_2$O | 7.6 |
|  | 2-Pyridyl | H | H | HCl, 5 H$_2$O | 5.7 |
| (−) | 2-chlorophenyl | H | H | HCl, 2 H$_2$O | 2.4 |
| (−) | Phenyl | H | H | HCl, 5 H$_2$O | 1.3 |

Reverse passive Arthus reaction (RPA) in rats

Charles Foster rats of both sexes, weighing 150–180 g, were sorted into groups of six animals each. 24 hours before the initiation of the RPA, the rats were shaved from the mid-dorsal region and fasted overnight. The test compounds were administered orally one hour before inducing the Arthus reaction. The RPA reaction was induced by intradermal injection of 0.1 ml of appropriately diluted rabbit anti-BSA serum. Immediately after the intradermal exposure, each rat received 0.5 ml of 0.4% bovine serum albumin intraveneously. Four hours after the intradermal challenge, each group of animals was killed by cervical dislocation. The full thickness of the skin was removed from the back of each animal, and a 12 mm diameter disk was punched out with a metal punch from the site of the antiserum injection. The wet weight of each skin site was determined as soon as possible. The edema caused by the RPA was measured as the difference (expressed in mg) between the wet weight of the site injected with antibody and that injected with normal rabbit serum.

The results are expressed as the percentage inhibition or potentiation of the edema by the compound as compared with the edema induced in the untreated control animals.

The results with representative compounds according to the invention and their salts are listed in Table 7.

TABLE 7

Action on the reverse passive Arthus reaction (RPA) on rats
Compound of the formula Ia

| cis | R$_1$ | R$_2$ | R$_5$ | X | DOSE mg/kg p.o. | % inhibition |
|---|---|---|---|---|---|---|
| (−) | CH$_3$ | H | CH$_2$—◁ | HCl.H$_2$O | 1.25 | — |
|  |  |  |  |  | 2.5 | 23.0 |
|  |  |  |  |  | 5.0 | 49.7 |
|  |  |  |  |  | 10.0 | — |
|  |  |  |  |  | 20.0 | 74.0 |
| (+) | CH$_3$ | H | CH$_3$ | HCl | 1.25 | 40.45 |
|  |  |  |  |  | 2.5 | 48.78 |
|  |  |  |  |  | 5.0 | 57.15 |
|  |  |  |  |  | 10.0 | 50.37 |
|  |  |  |  |  | 20.0 | 43.24 |
| (−) | CH$_3$ | H | CH$_3$ | HCl | 1.25 | 40.31 |
|  |  |  |  |  | 2.5 | 39.11 |
|  |  |  |  |  | 5.0 | 40.13 |
|  |  |  |  |  | 10.0 | 45.17 |
|  |  |  |  |  | 20.0 | 64.73 |
| (±) | CH$_3$ | H | CH$_3$ | HCl | 1.25 | 28.8 |
|  |  |  |  |  | 2.50 | 31.8 |
|  |  |  |  |  | 5.0 | 29.8 |
|  |  |  |  |  | 10.0 | 35.8 |
|  |  |  |  |  | 20.0 | 39.2 |
| (±) | C$_2$H$_5$ | H | CH$_3$ | HCl.1½H$_2$O | 1.25 | 16.0 |
|  |  |  |  |  | 2.5 | 34.31 |
|  |  |  |  |  | 5.0 | 41.65 |
|  |  |  |  |  | 10.0 | 43.60 |
|  |  |  |  |  | 20.0 | 77.10 |
| (±) | n-C$_3$H$_7$ | H | CH$_3$ | HCl.H$_2$O | 1.25 | 26.0 |
|  |  |  |  |  | 2.50 | 32.0 |
|  |  |  |  |  | 5.0 | 44.0 |
|  |  |  |  |  | 10.0 | 55.0 |
|  |  |  |  |  | 20.0 | 65.0 |

TABLE 7-continued

Action on the reverse passive Arthus reaction (RPA) on rats
Compound of the formula Ia

| cis | $R_1$ | $R_2$ | $R_5$ | X | DOSE mg/kg p.o. | % inhibition |
|---|---|---|---|---|---|---|
| (−) | n-$C_3H_7$ | H | $CH_3$ | $HCl.H_2O$ | 1.25 | — |
| | | | | | 2.5 | 42.7 |
| | | | | | 5.0 | 41.3 |
| | | | | | 10.0 | 63.7 |
| | | | | | 20.0 | 72.1 |
| (±) | Phenyl | H | $CH_3$ | $HCl.2H_2O$ | 1.25 | 57.5 |
| | | | | | 2.5 | 55.6 |
| | | | | | 5.0 | 68.1 |
| | | | | | 10.0 | 90.6 |
| | | | | | 20.0 | 95.7 |
| (±) | o-Chlorophenyl | H | $CH_3$ | $HCl.H_2O$ | 1.0 | 37.0 |
| | | | | | 2.0 | 60.0 |
| | | | | | 4.0 | 80.0 |
| (±) | 2,4-Dichloro-phenyl | H | $CH_3$ | $HCl.2.5 H_2O$ | 1.25 | 0 |
| | | | | | 2.5 | 41.7 |
| | | | | | 5.0 | 57.2 |
| | | | | | 10.0 | 49.5 |
| | | | | | 20.0 | 76.1 |
| (±) | p-Fluorophenyl | H | $CH_3$ | $HCl.H_2O$ | 1.25 | 24.4 |
| | | | | | 2.5 | 37.4 |
| | | | | | 5.0 | 61.5 |
| | | | | | 10.0 | 90.0 |
| | | | | | 20.0 | 86.2 |
| (±) | o-Fluorophenyl | H | $CH_3$ | $HCl.2H_2O$ | 1.25 | 0 |
| | | | | | 2.5 | 11.5 |
| | | | | | 5.0 | 52.7 |
| (±) | 2-Pyridyl | H | $CH_3$ | $HCl.1.5 H_2O$ | 1.25 | 0 |
| | | | | | 2.5 | 12.0 |
| | | | | | 5.0 | 43.0 |
| | | | | | 10.0 | 90.0 |
| | | | | | 20.0 | 90.0 |
| (−) | 2-Chlorophenyl | H | $CH_3$ | $HCl.1,5 H_2O$ | 1.25 | 34.0 |
| | | | | | 2.5 | 48.8 |
| | | | | | 5.0 | 70.0 |
| | | | | | 10.0 | 98.8 |
| | | | | | 20.0 | — |
| (−) | Phenyl | H | $CH_3$ | $HCl.\frac{1}{2}H_2O$ | 1.25 | — |
| | | | | | 2.5 | 26.2 |
| | | | | | 5.0 | 64.5 |
| | | | | | 10.0 | 92.2 |
| | | | | | 20.0 | — |

The invention is illustrated, but not restricted, by the examples which follow.

EXAMPLE 1

1-Methyl-4-(2,4,6-trimethoxyphenyl)-1,2,3,6-tetrahydropyridine

N-methylpiperidone (2.8 mol) is added with stirring to a solution of trimethoxybenzene (2.38 mol) in glacial acetic acid (750 ml), the temperature of the reaction mixture being maintained below 25° C. After the addition has ended, hydrogen chloride is bubbled through the reaction mixture, which is heated for 3 hours to 95°–100° C. and then concentrated, and the residue is diluted with water. The aqueous solution is extracted with ether, the ether is separated off and the aqueous layer is rendered alkaline with concentrated sodium hydroxide solution. The precipitate thus obtained is filtered off, washed with water and dried. Recrystallization from petroleum ether (60°–80° C.) gives 500 g of 1-methyl-3-(2,4,6-trimethoxyphenyl)-1,2,3,6-tetrahydropyridine of melting point 118°–122° C.

Analysis: calculated for $C_{15}H_{21}NO_3.0.5H_2O$: C, 66.17; H, 8.08; N, 5.14%. Found: C, 67.75; H, 7.56; N, 5.03%.

EXAMPLE 2

(±)-trans-3-Hydroxy-4-(2,4,6-trimethoxyphenyl)-1-methylpiperidine

A solution of $BF_3$ etherate (42 ml) in diethylene glycol dimethyl ether (42 ml) is added dropwise to a cooled mixture of 1-methyl-4-(2,4,6-trimethoxyphenyl)-1,2,3,6-tetrahydropyridine (20 g) and sodium borohydride (12 g) in diethylene glycol dimethyl ether (140 ml). The mixture is heated for one hour to 50° C., and the cooled reaction mixture is then treated with water (20 ml) and then with concentrated HCl (116 ml). The mixture is stirred for two hours at 50°–60° C., cooled and rendered alkaline with sodium hydroxide solution. Hydrogen peroxide solution (30%, 20 ml) is then added and the mixture is heated with stirring for two hours at 50°–60° C. The solution is cooled and extracted with ethyl acetate. The ethyl acetate extract is concentrated in vacuo. The residue is acidified with 2N HCl and extracted with ethyl acetate, and the organic layer is separated off. The aqueous layer is then rendered alkaline with sodium hydroxide solution and extracted with ether. The ether extract is washed with brine, dried over sodium sulfate and concentrated, a solid residue being obtained which is recrystallized from hot water, which gives trans-3- hydroxy-4-(2,4,6-trimethoxyphenyl)-1-methylpiperidine (12 g). Yield: 12 g; melting point 88°–89° C.

Analysis: compound as the oxalate, calculated for $C_{15}H_{23}NO_4 \cdot 0.5(COOH)_2 \cdot 1.75H_2O$: C, 56.5; H, 7.5; N, 4.12%. Found: C, 56.37; H, 8.14; N, 4.84%.

EXAMPLE 3

(+)-1-Methyl-4-(2,4,6-trimethoxyphenyl)-piperidin-3-one

Dimethyl sulfoxide (35 ml) is added dropwise under nitrogen to a solution, cooled to −60° C., of oxalyl chloride (20 ml) in dry methylene chloride (500 ml), and the mixture is stirred for 5–10 minutes. A solution of (±)-trans-3-hydroxy-4-(2,4,6-trimethoxyphenyl)-1-methylpiperidine (62 g) in methylene chloride (300 ml) is then added, while the temperature of the reaction mixture is held at −60° C. After the addition, the mixture is stirred for 15 minutes and triethylamine (155 ml) is added. The reaction mixture is then allowed to warm to a temperature of −30° C., diluted with water and rendered alkaline with sodium carbonate. The organic layer is separated off and the aqueous layer is extracted with ethyl acetate. The organic layers are combined, washed with brine, dried over anhydrous $Na_2SO_4$ and concentrated to give a solid residue which, on crystallization from isopropanol, gives the desired product (47 g) of melting point 110°–112° C.

Analysis: compound as the hydrochloride, calculated for $C_{15}H_{26}NO_4Cl$: C, 51.2; H, 7.39; N, 3.98; Cl, 10.09%. Found: C, 51.77; H, 7.16; N, 3.75; Cl, 11.45%.

EXAMPLE 4

(±)-cis-3-Hydroxy-4-(2,4,6-trimethoxyphenyl)-1-methylpiperidine

Sodium borohydride (10 g) is added with stirring to a solution, boiling under reflux, of 1-methyl-4-(2,4,6-trimethoxyphenyl)-piperidin-3-one in absolute ethanol. Stirring and heating under reflux is then continued for a further hour. On cooling, the reaction mixture is diluted with water, then concentrated in order to remove the ethanol and extracted with chloroform. The chloroform extract is washed with water, dried over anhydrous sodium sulfate and concentrated to give a solid residue which, on crystallization from acetone, gives the desired product (29.2 g) of melting point 124°–125° C.

Analysis: compound as the HCl salt; calculated for $C_{15}H_{24}NO_4Cl$: C, 56.69; H, 7.55; N, 4.4; Cl, 11.18%. Found: C, 56.78; H, 7.72; N, 3.93; Cl, 11.91%.

EXAMPLE 5

(±)-cis-3-Hydroxy-4-(3'-acetyl-4',6'-dimethoxy-2'-hydroxy)-phenyl-1-methylpiperidine $BF_3$ etherate (107.6 ml) is added dropwise, with cooling in an icebath, to a solution of cis-3-hydroxy-4-(2,4,6-trimethoxyphenyl)-1-methylpiperidine (35 g) in methylene chloride (500 ml). 76.2 ml of acetic anhydride are then added dropwise. Subsequently, the reaction mixture is stirred for 24 hours at room temperature, diluted with water, rendered alkaline with sodium carbonate and extracted with methylene chloride. The extract is concentrated and the residue (37 g) is dissolved in methanol (200 ml) and stirred for 2 hours with 5% aqueous potassium hydroxide solution (500 ml). The mixture is then concentrated in vacuo and the residue is extracted with chloroform. The residue obtained after concentrating the chloroform extract is then purified by chromatography over silica gel, cis-3-hydroxy-4-(3'-acetyl-4',6'-dimethoxy-2'-hydroxy)-phenyl-1-methylpiperidine (28 g) of melting point 215°–218° C. (as the HCl salt) being obtained.

Analysis: compound as the HCl salt, calculated for $C_{16}H_{24}NO_5Cl$: C, 55.57; H, 6.94; N, 4.05; Cl, 10.27%. Found: C, 55.24; H, 7.04; N, 3.88; Cl, 10.40%.

EXAMPLE 6

General procedure for preparing cis/trans-5,7-dimethoxy-2-($R_1$)-8-[4'-(3'-hydroxy-1-methyl)-piperidinyl]-4H-1-benzopyran-4-ones The solution of cis/trans-3-hydroxy-4-(3'-acetyl-4,6-dimethoxy-2'-hydroxy)-phenyl-1-methylpiperidine (1 equivalent) is stirred with a suitable ester (3 equivalents) and Na metal (~10 equivalents) or Na hydride (~5 equivalents) in dry dioxane or dimethylformamide at room temperature or at 70°–80° C. (see Table 8). Water is then added carefully and the mixture is extracted with chloroform. The organic phase is separated off, concentrated to some extent, saturated with HCl gas and then stirred for one hour. The solution is then rendered basic by addition of $Na_2CO_3$ and extracted with chloroform. The chloroform extract is dried over anhydrous $Na_2SO_4$, concentrated in vacuo and purified by means of column chromatography (over silica gel). Thin-layer chromatography (5% methanol in $CHCl_3$ + 1% by volume of $NH_4OH$: Rf value 0.5–0.7) can then be carried out.

Using the general procedure indicated, the compounds listed in Table 8 which follows in Example 6a were prepared:

TABLE 8

Preparation of cis/trans compounds of the formula Ie
$R_2 = H$, $R_4 = OH$, $R_8$ and $R_9 = CH_3$; free base)

| $R_1$ | Ester | Solvent | Base | Temp. | Melting point °C. |
|---|---|---|---|---|---|
| Methyl (±) | Ethyl acetate | Ethyl acetate | Na | Reflux | 236–38 |
| Methyl (+) | Ethyl acetate | Ethyl acetate | Na | Reflux | 228–29 |
| Methyl (−) | Ethyl acetate | Ethyl acetate | Na | Reflux | 228–30 |
| Ethyl (±) | Ethyl propionate | Ethyl propionate | Na | 70–80° C. | 240–42 (HCl) |
| n-Propyl (±) | Ethyl butyrate | Dioxane | Na | 70–80° C. | 196–97 |
| n-Propyl (+) | Ethyl butyrate | Dioxane | Na | 70–80° C. | 202–04 |
| n-Propyl (−) | Ethyl butyrate | Dioxane | Na | 70–80° C. | 202–04 |
| n-Butyl (±) | Ethyl valerate | Dioxane | Na | 70–80° C. | |
| Phenyl (±) | Methyl benzoate | DMF | NaH | RT | 232–34 (HCl) |
| Phenyl (−) | Methyl benzoate | DMF | NaH | RT | 225–27 |
| 2-Chlorophenyl (±) | Methyl 2-chlorobenzoate | DMF | NaH | RT | 190–91 (HCl) |
| 2-Chlorophenyl (−) | Methyl 2-chlorobenzoate | DMF | NaH | RT | 110 |
| p-Bromophenyl (±) | Methyl 2-bromobenzoate | DMF | NaH | RT | 167–70 |
| p-Chlorophenyl (±) | Methyl 2-chlorobenzoate | DMF | NaH | RT | |
| 2,4-Dichlorophenyl (±) | Methyl 2,4-dichlorobenzoate | DMF | NaH | RT | 179–81 (HCl) |

TABLE 8-continued

Preparation of cis/trans compounds of the formula Ie
$R_2 = H, R_4 = OH, R_8$ and $R_9 = CH_3$; free base)

| $R_1$ | Ester | Solvent | Base | Temp. | Melting point °C. |
|---|---|---|---|---|---|
| 2-Fluorophenyl (±) | Methyl 2-fluorobenzoate | DMF | NaH | RT | |
| 4-Fluorohenyl (±) | Methyl 4-fluorobenzoate | DMF | NaH | RT | 212–14 |
| 4-Methylphenyl (±) | Methyl 4-methylbenzoate | DMF | NaH | RT | 185 |
| 2-Pyridyl (±) | Methyl picolinate | DMF | NaH | RT | 208–10 |
| 4-Pyridyl (±) | Methyl isonicotinate | DMF | NaH | | 215–17 |

EXAMPLE 6a cis-5,7-Dimethoxy-2-methyl-8-[4'-(3'-hydroxy-1'-methyl)-piperidinyl]-4H-1-benzopyran-4-one A solution of cis-3-hydroxy-4-(3'-acetyl-4',6'-dimethoxy-2'-hydroxy)-phenyl-1-methylpiperidine (10 g) in ethyl acetate (500 ml) is heated to reflux, and sodium (7 g) is added in small portions. The mixture is stirred and heated for 2 to 3 hours under reflux. After cooling, the mixture is diluted with water and the organic layer is separated off. The latter is then concentrated to half the volume, treated with concentrated HCl (10 ml) and stirred for about one hour. The mixture is then diluted with water, and the aqueous layer is rendered alkaline with $Na_2CO_3$ and extracted with chloroform. The chloroform extract is dried over anhydrous $Na_2SO_4$, concentrated in vacuo and purified by column chromatography over silica gel, the desired product (8 g) being obtained. Recrystallized from chloroform/petroleum ether, melting point 236°–238° C. (HCl salt).

Analysis: compound as the dihydrochloride, calculated for $C_{18}H_{25}NO_5Cl_2$: C, 50.46; H, 6.66; N, 2.68; Cl, 15.87%. Found: C, 49.80; H, 6.77; N, 3.27; Cl, 16.35%.

EXAMPLE 7

General demethylation procedure for the preparation of cis/trans-5,7-dihydroxy-2-($R_1$)-8-[4'-(3'-hydroxy-1'-methyl)-piperidinyl]-4H-1-benzopyran-4-one hydrochlorides:

Dimethoxychromone (1.0 g), pyridine hydrochloride (5–10 g) and quinoline (0.5 ml) are mixed and heated for 2–3 hours to 180°–190° C. The reaction mixture is then allowed to cool, water (1 ml) is added and the mixture is rendered basic by addition of solid sodium bicarbonate. The semi-solid product is thoroughly extracted with 20% methanol in chloroform, and the organic phase is concentrated and purified by means of column chromatography (silica gel; 15% by volume of methanol in chloroform, with 1% by volume of added $NH_4OH$, as the eluent; Rf: 0.4–0.7). The hydrochloride salt is obtained by treatment with ethereal HCl.

Using the general procedure indicated, the compounds listed in Table 9 which follows and in Example 7a are prepared:

TABLE 9

(Formula Ie with $R_2 = R_8 = R_9 = H, R_4 = OH$)

| $R_1$ | X | Melting point °C. | $[\alpha]_D{}^{20}$ |
|---|---|---|---|
| Methyl | HCl | 237–240 | (±) |
| Methyl | HCl | 243 | +29.5° |
| Methyl | HCl | 241–242 | −27.5° |
| Ethyl HCl 1.5H₂O | | 230–233 | (±) |
| n-Propyl | HCl, H₂O | 190–192 | (±) |
| n-Propyl | HCl, 0.5H₂O | 197–200 | +33.01° |
| n-Propyl | HCl, 0.5H₂O | 198–201 | −25.91 |
| Phenyl | HCl, 2H₂O | 273–275 | (±) |
| Phenyl | HCl, H₂O | 266–269 | −50.4° |
| 2-Chlorophenyl | HCl, H₂O | 198–200 | (±) |
| 2-Chlorophenyl | HCl, 1.5H₂O | 190–194 | −3.4° |
| 4-Bromophenyl | HCl, 2H₂O | 215 | (±) |
| 4-Chlorophenyl | HCl, 1.5H₂O | 225 | (±) |
| 2,4-Dichlorophenyl | HCl, 2.5H₂O | 165–166 | (±) |
| 2-Fluorophenyl | HCl, 2H₂O | 263–265 | (±) |
| 4-Fluorophenyl | HCl, H₂O | 285–287 | (±) |
| 4-Methylphenyl | HCl, 1.5H₂O | 247–249 | (±) |
| 2-Pyridyl | HCl, 1.5H₂O | 229 | (±) |
| 4-Pyridyl | 2HCl, 2H₂O | 278–280 | (±) |

EXAMPLE 7a cis-5,7-Dihydroxy-2-methyl-8-[4'-(3'-hydroxy-1'-methyl)-piperidinyl]-4H-1-benzopyran-4-one hydrochloride cis-5,7-Dimethoxy-2-methyl-8-[4'-(3'-hydroxy-1'-methyl)-piperidinyl]-4H-1-benzopyran-4-one (1.2 g), pyridine hydrochloride (8.0 g) and quinoline (0.5 ml) are mixed and heated for 2.5 hours to 180°–190° C. The mixture is cooled, water (1 ml) is added and the mixture is rendered alkaline by addition of solid sodium bicarbonate, and the semisolid product is thoroughly extracted with 20% methanol in chloroform. The organic layer is concentrated and purified by column chromatography over silica gel with 15% methanol in chloroform, containing 1% of $NH_4OH$, as the eluent. The product thus obtained is treated with ethereal HCl, giving the hydrochloride, yield 1.05 g, melting point 237°–240° C.

Analysis: compound as the HCl salt, calculated for $C_{16}H_{20}NO_5Cl$: C, 54.6; H, 6.07; N, 4.24; Cl, 10.77%. Found: C, 55.62; H, 6.49; N, 3.59; Cl, 9.84%.

EXAMPLE 8

Resolution of (±)-cis-3-hydroxy-1-methyl-4-(2,4,6-trimethoxyphenyl)-piperidine

The racemic cis-3-hydroxy compound (90 g) is dissolved in methanol (300 ml), (−)-dibenzoyltartaric acid (126.4 g) in methanol (200 ml) is added, and the mixture is heated to the boil. Diisopropyl ether (about 500 ml) is then slowly added and the clear solution is allowed to cool, the tartrate salt crystallizing out slowly. The latter is filtered off and recrystallized five times from methanol/diisopropyl ether, $[\alpha]_D{}^{20} = +48.3°$ (MeOH). The tartrate salt (43 g) is suspended in water (200 ml), hydrochloric acid (2N, 100 ml) is added, and the mixture is stirred. The reaction mixture is extracted with five times 100 ml of ethyl acetate. The tartaric acid is recovered from the ethyl acetate extract. The aqueous layer is rendered alkaline with sodium carbonate and extracted with chloroform. The chloroform extract is dried over anhydrous sodium sulfate and concentrated, the (+)-3-hydroxy compound, 17.7 g, melting point 109°–111° C., $[\alpha]_D^{20}=+53.81°$ (methanol), being obtained. The filtrates from the tartrate crystallizations are combined, and the free base is recovered as described above. The free base (20 g) is dissolved in methanol (110 ml), (+)-dibenzoyltartaric acid (29 g) is added, and the solution is heated to the boil. Diisopropyl ether (110 ml) is then added slowly. On standing at room temperature, the tartrate crystallizes out. It is filtered off and recrystallized three times from a methanol/diisopropyl ether mixture. Yield: 20.2 g, $[\alpha]_D^{20}=-49°$ (MeOH). The free base is isolated as described above, yield: 8.2 g, melting point 109°–111° C., $[\alpha]_D^{20}=-54.13°$ (methanol).

Optically pure isomers were prepared from optically pure (+)- or (−)-cis-3-hydroxy-4-(3-acetyl-4,6-dimethoxy-2-hydroxy)-phenyl-1-methylpiperidine as in Examples 9 and 10 which follow:

EXAMPLE 9

(−)-cis-3-Hydroxy-4-(3'-acetyl-4',6'-dimethoxy-2'-hydroxy)-phenyl-1-methylpiperidine (−)-cis-3-Hydroxy-4-(2',4',6'-trimethoxyphenyl)-1-methyl-piperidine is treated in the same way as in Example 5, giving (−)-cis-3-hydroxy-4-(3'-acetyl-4',6'-dimethoxy-2'-hydroxy)-phenyl-1-methylpiperidine of melting point 184°–86° C., $[\alpha]_D^{20}=-32.63°$ (MeOH, c=0.614).

EXAMPLE 10

(+)-cis-3-Hydroxy-4-(3'-acetyl-4',6'-dimethoxy-2'-hydroxy)-phenyl-1-methylpiperidine (+)-cis-3-Hydroxy-4-(2',4',6'-trimethoxyphenyl)-1-methylpiperidine is treated in the same way as in Example 5, giving (+)-cis-3-hydroxy-4-(3'-acetyl-4',6'-dimethoxy-2'-hydroxy)-phenyl-1-methylpiperidine of melting point 184°–85° C., $[\alpha]_D^{20}=+34.47°$ (MeOH, c=0.586).

EXAMPLE 11

(−)-cis-5,7-Dimethoxy-2-methyl-8-[4'-(3'-hydroxy-1'-methyl)-piperidinyl]-4H-1-benzopyran-4-one (−)-cis-3-Hydroxy-4-(3'-acetyl-4',6'-dimethoxy-2'-hydroxy)-phenyl-1-methylpiperidine is treated in the same way as in Example 6, giving (−)-cis-5,7-dimethoxy-2-methyl-8-[4'-3'-hydroxy-1'-methyl)-piperidinyl]-4H-1-benzopyran-4-one of melting point 228°–30° C., $[\alpha]_D^{20}=-80.59°$ (MeOH, c=0.59).

EXAMPLE 12

(+)-cis-5,7-Dimethoxy-2-methyl-8-[4'-(3'-hydroxy-1'-methyl)-piperidinyl]-4H-1-benzopyran-4-one (+)-cis-3-Hydroxy-4-(3'-acetyl-4',6'-dimethoxy-2'-hydroxy)-phenyl-1-methylpiperidine is treated in the same way as in Example 6, giving (+)-cis-5,6-dimethoxy-2-methyl-8-[4'-(3'-hydroxy-1'-methyl)-piperidinyl]-4H-1-benzopyran-4-one of melting point 228°–29° C., $[\alpha]_D^{20}=+84.1°$ (MeOH, c=0.618).

EXAMPLE 13

(−)-cis-5,7-Dihydroxy-2-methyl-8-[4'-(3'-hydroxy-1'-methyl)-piperidinyl]-4H-1-benzopyran-4-one hydrochloride (−)-cis-5,7-Dimethoxy-2-methyl-8-[4'-(3'-hydroxy-1'-methyl)-piperidinyl]-4H-1-benzopyran-4-one is treated in the same way as in Example 7, giving (−)-cis-5,7-dihydroxy-2-methyl-8-[4'-(3'-hydroxy-1'-methyl)-piperidinyl]-4H-1-benzopyran-4-one hydrochloride of melting point 242°–45° C., $[\alpha]_D^{20}=-25.37°$ (MeOH, c=0.653).

EXAMPLE 14

(+)-cis-5,7-Dihydroxy-2-methyl-8-[4'-(3'-hydroxy-1'-methyl)-piperidinyl]-4H-1-benzopyran-4-one hydrochloride (+)-cis-5,7-Dimethoxy-2-methyl-8-[4'-(3'-hydroxy-1'-methyl)-piperidinyl]-4H-1-benzopyran-4-one is treated in the same way as in Example 7, giving (+)-cis-5,7-dihydroxy-2-methyl-8-[4'-(3'-hydroxy-1'-methyl)-piperidinyl]-4H-1-benzopyran-4-one hydrochloride of melting point 242°–44° C., $[\alpha]_D^{20}=+29.57°$ (MeOH, c=0.58).

EXAMPLE 15 cis-5,7-Dihydroxy-2-ethyl-8-[4'-(3'-hydroxy-1'-methyl)-piperidinyl]-4H-1-benzopyran-4-one hydrochloride cis-3-Hydroxy-4-(3'-acetyl-4',6'-dimethoxy-2'-hydroxy)-phenyl-1-methylpiperidine is treated in Example 6 with ethyl propionate in place of ethyl acetate, and the product is demethoxylated as described in Example 7, giving cis-5,7-dihydroxy-2-ethyl-8-[4'-(3'-hydroxy-1'-methyl)-piperidinyl]-4H-1-benzopyran-4-one hydrochloride of melting point 230°–33°.

Analysis: calculated for $C_{19}H_{25}NO_5.HCl0.5H_2O$: C, 53.3; H, 6.53; N, 3.66; Cl, 9.28%. Found: C, 53.1; H, 6.51; N, 3.83; Cl, 9.45%.

EXAMPLE 16 cis-5,7-Dihydroxy-2-n-propyl-8-[4'-(3'-hydroxy-1'-methyl)-piperidinyl]-4H-1-benzopyran-4-one hydrochloride cis-3-Hydroxy-4-(3'-acetyl-4',6'-dimethoxy-2'-hydroxy)-phenyl-1-methylpiperidine is treated as in Example 6 with ethyl butyrate in place of ethyl acetate, and the product is demethoxylated as described in Example 7, giving cis-5,7-dihydroxy-2-n-propyl-8-[4'-(3'-hydroxy-1'-methyl)-piperidinyl]-4H-1-benzopyran-4-one hydrochloride of melting point 190°–92° C.

Analysis: calculated for $C_{20}H_{27}NO_5.HCl.H_2O$: C, 55.74; H, 6.70; N, 3.61; Cl, 9.16%. Found: C, 56.25; H, 6.65; N, 3.52; Cl, 9.39%.

EXAMPLE 17 cis-(−)-5,7-Dihydroxy-2-methyl-8-[4'-(3'-hydroxy)-piperidinyl]-4H-benzopyran-4-one cis-(−)-5,7-Dihydroxy-2-methyl-8-[4'-(3'-hydroxy-1'-methyl)-piperidinyl]-4H-1-benzopyran-4-one (5 g) is heated for 12 hours to 90° C. with acetic anhydride (25 ml) and sodium acetate (4.5 g). The acetic anhydride is distilled off in a high vacuum and the residue is stirred up with ethyl acetate. The fraction soluble in ethyl acetate is concentrated to dryness. The residue is dissolved in dry chloroform (27 ml), anhydrous potassium carbonate (5 g) is added and the mixture is cooled to 0° C. Cyanogen bromide (6 g) in dry chloroform (25 ml) is added dropwise. After the addition, the reaction mixture is stirred for 4–5 hours at 40°–50° C. and filtered, and the filtrate is washed with a small quantity of brine, dried over anhydrous sodium sulfate and concentrated. The residue is heated for 7–8 hours with 1N hydrochloric acid (30 ml) on a steam bath. The reaction mixture is rendered alkaline by addition of solid sodium carbonate and concentrated. The residue is allowed to run through an HP-20 column, and the product is eluted with 20% MeOH in H$_2$O. The product is crystallized from MeOH/diisopropyl ether, melting point 300° C., $[\alpha]_D^{20}=-11.38°$ (MeOH, c=0.9).

Analysis: compound as the hydrochloride salt, calculated for C$_{15}$H$_{18}$NO$_5$Cl: C, 55.00; H, 5.53; N, 4.27; Cl, 10.81%. Found: C, 54.33; H, 5.59; N, 3.93; Cl, 11.21%.

EXAMPLE 18 cis-(−)-5,7-Dihydroxy-2-methyl-8-[4′-(1′-cyclopropylmethyl-3′-hydroxy)-piperidinyl]-4H-1-benzopyran-4-one hydrochloride cis-(−)-5,7-Dihydroxy-2-methyl-8-[4′-(3′-hydroxy)-piperidinyl]-4H-1-benzopyran-4-one (1.0 g), cyclopropyl methyl ketone (1.5 ml), isobutanol (15 ml) and potassium carbonate (3 g) are mixed and heated for 15 hours to 90° C. The reaction mixture is filtered and the residue is washed with chloroform. The filtrate is concentrated and purified by column chromatography over silica gel. The compound is eluted with 6% MeOH in chloroform. The hydrochloride is prepared by addition of ethereal HCl, yield 0.7 g, melting point 249°–51° C., $[\alpha]_D^{20}=-35.4°$ (MeOH, c=0.571).

Analysis: calculated for C$_{19}$H$_{26}$NO$_6$Cl: C, 57.07; H, 6.51; N, 3.75; Cl, 8.87%. Found: C, 57.18; H, 6.51; N, 3.75; Cl, 9.44%.

We claim:

1. A compound of the formula I

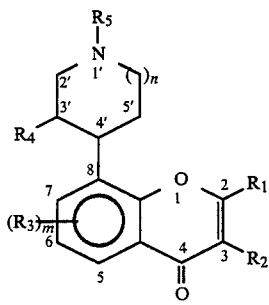

in which:
R$_1$ is hydrogen, unsubstituted C$_1$–C$_6$-alkyl, C$_1$–C$_6$ alkyl substituted by halogen, hydroxy or carboxy, phenyl-C$_1$–C$_4$-alkyl wherein the phenyl is unsubstituted or mono- or polysubstituted by halogen, C$_1$–C$_4$-alkyl, C$_1$–C$_4$-alkoxy, nitro or trifluoromethyl, C$_3$–C$_6$-cycloalkyl, C$_3$–C$_6$-cycloalkyl-C$_1$–C$_4$-alkyl, C$_2$–C$_6$-alkenyl, C$_3$–C$_6$-alkynyl, phenyl which is unsubstituted or mono- or polysubstituted by halogen, C$_1$–C$_4$-alkyl, C$_1$–C$_4$-alkoxy, nitro, trifluoromethyl, amino or hydroxy, or is carboxyl, an aldehyde or -COO-C$_1$–C$_4$-alkyl group, or 2- or 4-pyridyl, R$_2$ is hydrogen, C$_1$–C$_6$-alkyl, nitro, amino, di-C$_1$–C$_4$-alkylamino or di-C$_1$–C$_4$-alkylaminomethyl or a halogen atom, R$_3$ is unsubstituted C$_1$–C$_4$-alkyl, C$_1$–C$_4$-alkyl substituted by halogen, hydroxy or carboxy, hydroxyl, C$_1$–C$_4$-alkoxy, phenyl-C$_1$–C$_4$-alkyl wherein the phenyl is unsubstituted or mono- or polysubstituted by halogen, C$_1$–C$_4$-alkyl, C$_1$–C$_4$-alkoxy, nitro or trifluoromethyl, nitro, halogen, amino, C$_1$–C$_4$-alkylamino or di-C$_1$–C$_4$-alkylamino, R$_4$ is hydrogen, hydroxyl, C$_1$–C$_4$-alkoxy, C$_1$–C$_4$-alkanoyloxy, C$_1$–C$_4$-alkoxycarbonyl, phenoxy which is unsubstituted or mono- or polysubstituted by halogen, C$_1$–C$_4$-alkyl, C$_1$–C$_4$-alkoxy, nitro or trifluoromethyl, amino, C$_1$–C$_4$-alkylamino or di-(C$_1$–C$_4$-alkyl)-amino, R$_5$ is hydrogen, unsubstituted C$_1$–C$_6$-alkyl, C$_1$–C$_6$-alkyl substituted by halogen, hydroxy or carboxy, phenyl-C$_1$–C$_4$-alkyl wherein the phenyl is unsubstituted or mono- or polysubstituted by halogen, C$_1$–C$_4$-alkyl, C$_1$–C$_4$-alkoxy, nitro or trifluoromethyl, C$_3$–C$_6$-cycloalkyl, C$_3$–C$_6$-cycloalkyl-C$_1$–C$_4$-alkyl, C$_1$–C$_4$-alkanoyl or phenylcarbonyl which is unsubstituted or mono- or polysubstituted by halogen, C$_1$–C$_4$-alkyl, C$_1$–C$_4$-alkoxy, nitro or trifluoromethyl, n is an integer between 0 and 2 and m is an integer between 0 and 3, with the exception of the compound 5,7-dihydroxy-2-methyl-8-[4′-(3′-hydroxy-1′-methyl)-piperidinyl]-4H-1-benzopyran-4-one, or a pharmacologically acceptable acid addition salt or optical isomer thereof.

2. A compound as claimed in claim 1, wherein R$_1$, R$_2$ and R$_5$ are as defined, R$_3$ and R$_4$ are a hydroxyl group, m is the number 2 and n is the number 1.

3. A compound as claimed in claim 1, wherein R$_1$ is hydrogen or C$_1$–C$_3$-alkyl, R$_2$ is hydrogen or C$_1$–C$_3$-alkyl, R$_3$ and R$_4$ are each a hydroxyl group, R$_5$ is C$_1$–C$_3$-alkyl or C$_3$–C$_5$-cycloalkyl, m is the number 2 and n is the number 1.

4. cis-(±)-2-(2-Chlorophenyl)-5,7-dihydroxy-8-[4′-(3′-hydroxy-1′-methyl)-piperidinyl]-4H-1-benzopyran-4-one or a pharmacologically acceptable acid addition salt thereof.

5. cis-(−)-2-(2-Chlorophenyl)-5,7-dihydroxy-8-[4′-(3′-hydroxy-1′-methyl)-piperidinyl]-4H-1-benzopyran-4-one or a pharmacologically acceptable acid addition salt thereof.

6. cis-(−)-2-Phenyl-5,7-dihydroxy-8-[4′-(3′-hydroxy-1′-methyl)-piperidinyl]-4H-1-benzopyran-4-one or a pharmacologically acceptable acid addition salt thereof.

7. cis-(±)-2-Phenyl-5,7-dihydroxy-8-[4′-(3′-hydroxy-1′-methyl)-piperidinyl]-4H-1-benzopyran-4-one or a pharmacologically acceptable acid addition salt thereof.

8. cis-(±)-2-(p-Fluorophenyl)-5,7-dihydroxy-8-[4′-(3′-hydroxy-1′-methyl)-piperidinyl]-4H-1-benzopyran-4-one or a pharmacologically acceptable acid addition salt thereof.

9. cis-(±)-2-(2-Pyridyl)-8-[4′-(3′-hydroxy-1′-methyl)-piperidinyl]-4H-benzopyran-4-one or a pharmacologically acceptable acid addition salt thereof.

10. A pharmaceutical composition comprising a pharmaceutically effective amount of a compound of the formula I as claimed in claim 1, or a pharmacologically acceptable acid addition salt thereof, and a pharmaceutically acceptable carrier.

11. A method for the treatment of a human or animal in need of anti-inflammatory or immunomodulating action which comprises administering to said human or animal an amount effective for said treatment of the pharmaceutical composition as claimed in claim 10.

12. A method for the treatment of a human or animal in need of anti-inflammatory or immunomodulating action which comprises administering to said human or animal an amount effective for said treatment of a compound of the formula I as claimed in claim 1.

* * * * *

UNITED STATES PATENT AND TRADEMARK OFFICE
CERTIFICATE OF CORRECTION

PATENT NO. : 4,900,727

DATED : February 13, 1990

INVENTOR(S) : Samba L. KATTIGE et al.

It is certified that error appears in the above-identified patent and that said Letters Patent is hereby corrected as shown below:

ON THE TITLE PAGE

Section [54], line 3 should read --IMMUNOMODULATING ACTION--.

Section [57], in the Abstract, line 19 from the bottom: "arly-$C_1$-$C_4$-alkyl" should read --aryl-$C_1$-$C_4$-alkyl--.

Section [57], in the Abstract, line 10 from the bottom: "$C_1$-$C_4$-alkyoxy, $C_1$-$C_4$-alkyoxycarbonyl" should read --$C_1$-$C_4$-alkoxy, $C_1$-$C_4$-alkanoyloxy, $C_1$-$C_4$-alkoxycarbonyl--.

In Column 1, line 3 of the title should read --IMMUNOMODULATING ACTION--.

UNITED STATES PATENT AND TRADEMARK OFFICE
CERTIFICATE OF CORRECTION

PATENT NO. : 4,900,727  Page 2 of 3
DATED : February 13, 1990
INVENTOR(S) : Samba L. KATTIGE et al.

It is certified that error appears in the above-identified patent and that said Letters Patent is hereby corrected as shown below:

In Fig. 2, structure IA should appear as follows:

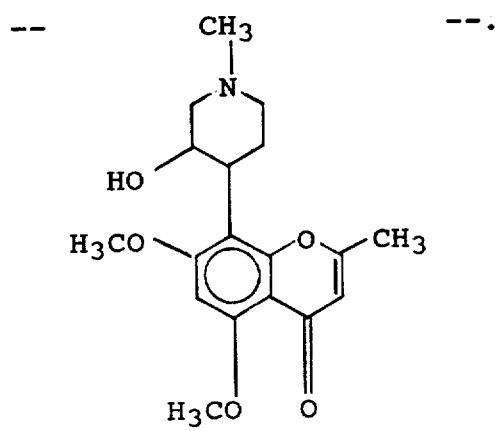

In Column 7, line 57: "VIII" should read --VIIIA--.

UNITED STATES PATENT AND TRADEMARK OFFICE
CERTIFICATE OF CORRECTION

PATENT NO. : 4,900,727
DATED : February 13, 1990
INVENTOR(S) : Samba L. KATTIGE et al.

It is certified that error appears in the above-indentified patent and that said Letters Patent is hereby corrected as shown below:

In column 9, line 10 should read --of the formula XIIA with R=Ac is esterfied using a--.

Signed and Sealed this

Twenty-ninth Day of June, 1993

Attest:

MICHAEL K. KIRK

Attesting Officer

Acting Commissioner of Patents and Trademarks